(12) United States Patent  
Harper

(10) Patent No.: US 8,617,165 B2  
(45) Date of Patent: Dec. 31, 2013

(54) ROD REDUCING INSTRUMENT AND METHODS OF USE THEREOF

(75) Inventor: Michael Harper, Pottstown, PA (US)

(73) Assignee: Globus Medical, Inc., Audubon, PA (US)

( * ) Notice: Subject to any disclaimer, the term of this patent is extended or adjusted under 35 U.S.C. 154(b) by 287 days.

(21) Appl. No.: 12/874,002

(22) Filed: Sep. 1, 2010

(65) Prior Publication Data

US 2012/0053643 A1 Mar. 1, 2012

(51) Int. Cl.  
*A61B 17/70* (2006.01)

(52) U.S. Cl.  
USPC .................................................. 606/86 A

(58) Field of Classification Search  
USPC .............................. 606/86 A, 99, 914  
See application file for complete search history.

(56) References Cited

U.S. PATENT DOCUMENTS

2008/0243190 A1* 10/2008 Dziedzic et al. ............... 606/278  
2009/0228054 A1* 9/2009 Hoffman et al. ............ 606/86 A

* cited by examiner

*Primary Examiner* — Sameh Boles

(57) ABSTRACT

The invention encompasses instrumentation for rod reduction for use in orthopedic surgery that is ergonomic and intuitive to use. In certain embodiments, the invention encompasses a rod reducing instrument including a series of ratcheting mechanisms that reduces the need for large applications of manual force for rod positioning necessary during surgical procedures. The internalized mechanism also allows for a reduction in fine increments without an increase in surgical instrument profile or necessary force input. In certain embodiments, the instrument includes one or more channels to accept the locking delivery instrument further streamlining the surgical process. The rod reducing instrument of the invention refines the reduction process allowing for faster, stronger reduction, with a quick and effective release.

35 Claims, 7 Drawing Sheets

ROD REDUCING INSTRUMENT AND METHODS OF USE THEREOF

FIELD OF THE INVENTION

The invention encompasses instrumentation for rod reduction for use in orthopedic surgery that is ergonomic and intuitive to use. In certain embodiments, the invention encompasses a rod reducing instrument including a series of ratcheting mechanisms that reduces the need for large applications of manual force for rod positioning necessary during surgical procedures. The internalized mechanism also allows for a reduction in fine increments without an increase in surgical instrument profile or necessary force input. In certain embodiments, the instrument includes one or more channels to accept the locking delivery instrument further streamlining the surgical process. The rod reducing instrument of the invention refines the reduction process allowing for faster, stronger reduction, with a quick and effective release.

BACKGROUND OF THE INVENTION

In the field of orthopedic surgery, and particularly spinal surgery, injury, malformation, or other defect can be corrected by implanting a rod affixed to the body part to be corrected. For example, rod systems have been developed for correcting the positioning of and stabilizing the spine, and for facilitating fusion at various levels of the spine. In one such system, a rod is disposed longitudinally along a length of the spine. The rod is preferably bent, either prior to or during surgery, to correspond to the normal curvature of the spine in the particular region being instrumented, or to such other curvature as the surgeon may deem appropriate to correct the defect. For example, the rod can be bent to form a normal kyphotic curvature for the thoracic region of the spine, or to form a normal lordotic curvature for the lumbar region. The rod is engaged to a number of fixation elements fixed to or engaged with the vertebrae along the segment of the spinal column.

A variety of fixation elements can be provided that are configured to engage the vertebrae. For instance, one such fixation element is a laminar hook, configured to engage a lamina of the vertebra. Another prevalent fixation element is a spinal screw, which can be threaded into a pedicle or other portion of vertebral bone.

In one typical spinal procedure, an elongated implant (e.g., a rod) is coupled to two or more fixation elements (e.g., bone screws) that are fixed to opposite sides of the spine or spinous processes. The bone screws are first threaded into a portion of several vertebral bodies, such as the pedicles of these vertebrae. The rod is coupled to the bone screws to provide corrective and stabilizing forces to the spine. Affixing a rod to a bone screw generally requires the rod to be in close adjacent position or in contact with the screw.

Rod reduction is commonly performed by a surgeon using his or her hands and/or rigid tools such as pliers, levers or other instrumentation adaptable to create the necessary pushing and/or pulling forces on the implanted screw and rod. Such procedures generally require the surgeon to place the rod directly over the implanted fixation element, intersecting a longitudinal axis of the fixation element. Consequently, access to the rod and the implanted fixation element along that axis (i.e., directly above the opening in the fixation element into which the rod is to be placed) is necessary or at least highly desirable. However, such access can be difficult depending on such factors as the malformation to be corrected and the overall physiology of the patient, and can be very difficult in procedures in which surgical invasiveness is to be minimized, as a result of the small ports or incisions of such procedures. Additionally, with use of mono-axial screws, the physiology of the patient can require that the screw be placed at an angle such that the surgeon would have difficulty accessing and exerting force in the necessary orientation on the rod and/or fixation element. With multi-axial fixation devices, the orientation of an unsecured rod-receiving part of the fixation element can be even more varied with respect to the rod and/or the surgeon. Consequently, the surgeon is still frequently faced with the task of reducing a rod from an awkward angle.

The inventors have developed a rod reducing instrument that can be used efficiently, safely and securely in rod reduction procedures and can be used in both minimally invasive (e.g., laproscopic) and open surgical approaches to the site of rod attachment.

SUMMARY OF THE INVENTION

The invention encompasses instrumentation for rod reduction during surgery, for example, orthopedic surgery that is efficient and convenient to use. The instruments overcome the requirement for direct application of manual force to a rod to position it in a desired location relative to a fastener. The instruments can also facilitate attachment of the rod to the fastener, and have application in both open surgical procedures and minimally invasive surgical procedures.

Accordingly, in one embodiment, the invention encompasses an instrument and method for guiding a spinal rod into an orthopedic implant. The instrument may be held and operated using one hand, thereby facilitating insertion and securing of a spinal rod in a selected position. The instrument includes, inter alia, a main body; a drive handle; a reduction arm; a reduction pawl; a retention pawl; a main release; a drive release; and a ratchet collet.

The ratchet collet portion holds a rod in place until the surgeon inserts a set screw or other device for securing the rod to the anchor. The ratchet collet further defines a path for inserting and securing a locking device, such as a set screw, for securing the rod in the implant while also holding the rod in the implant. The path for the screw is aligned with the rod-holding portion of the implant. Using the instrument, a surgeon can guide a rod into a selected position in the implant, reposition the spine to match the contour of the rod, hold the rod in the selected position and secure the rod to the implant.

According to one embodiment of the invention, an instrument for guiding a spinal rod into an implant is provided. The instrument comprises a main body; a drive handle; a reduction arm; a reduction pawl; a retention pawl; a main release; a drive release; and a ratchet collet. The instrument further includes a first channel proximal to a main body handle and a second channel proximal to the ratchet collet. The channels define a path for inserting a locking mechanism to lock the spinal rod into the rod-receiving portion.

According to another embodiment of the invention, an instrument for guiding a spinal rod into an implant comprises a main body including a first handle and a drive handle pivotally coupled to the main body at a first hinge point. The instrument further includes a first channel in the main body adjacent to the first handle and a second channel on the main body adjacent to the ratchet collet. The instrument further includes an internal actuating assembly comprising a reduction arm, a reduction pawl, a retention pawl, and a drive release.

BRIEF DESCRIPTION OF THE FIGURES

A more complete understanding of the present invention may be obtained by reference to the accompanying drawings, when considered in conjunction with the subsequent detailed description. The embodiments illustrated in the drawings are intended only to exemplify the invention and should not be construed as limiting the invention to the illustrated embodiments, in which.

DETAILED DESCRIPTION OF THE INVENTION

Figure 1:
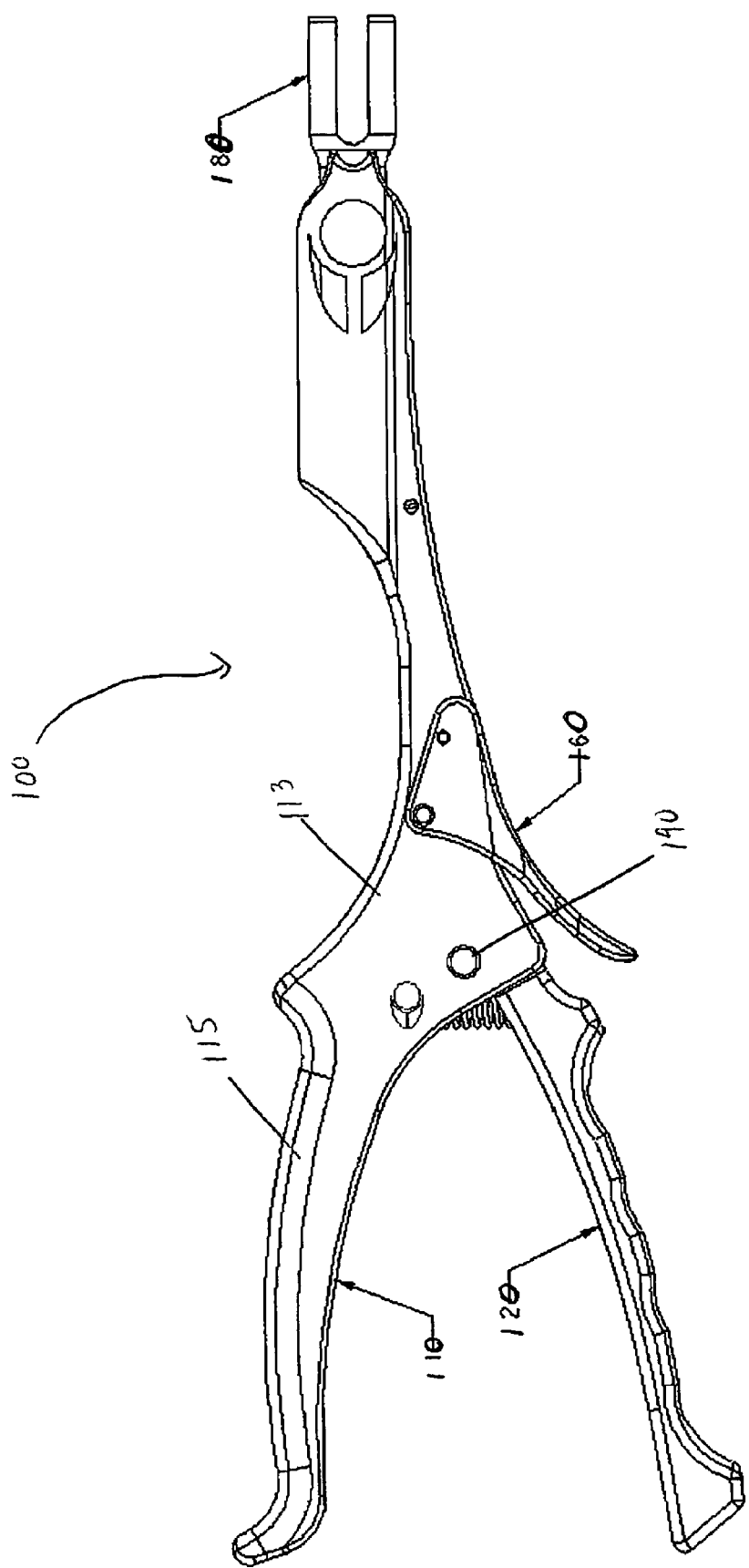
FIG. 1 illustrates a side perspective view of a rod reduction instrument in accordance with one illustrative embodiment of the invention.

The invention generally encompasses instrumentation for rod reduction for use in orthopedic surgery that is ergonomic and intuitive to use. The instrument of the invention is useful for a surgeon to insert during a spinal procedure a spinal fixation element, such as a spinal rod, into an implant, such as a polyaxial screw, hook or other fastener device used in a spinal fixation system, according to an illustrative embodiment of the invention. The illustrative instrument is configured for engaging and seating a spinal rod in a rod-receiving portion of a polyaxial screw, though one skilled in the art will recognize that the instrument may be used for any suitable surgical device.

The invention generally encompasses an orthopedic instrument for reducing a rod comprising: a main body; a drive handle; a reduction arm; a reduction pawl; a retention pawl; a main release; a drive release; and a ratchet collet.

In certain illustrative embodiments, the main body comprises a palm handle, a mechanism housing, and a collet compressor.

In certain illustrative embodiments, the drive handle is secured to the main body, directly opposing the main body palm handle, forming an actuating grip assembly.

In certain illustrative embodiments, the instrument includes an actuating assembly located within the main body. In certain illustrative embodiments, the actuating assembly includes a reduction arm, a reduction pawl, a retention pawl, and a drive release.

In certain illustrative embodiments, the drive handle is secured to a first end of the reduction arm, offset from a central pivot point.

In certain illustrative embodiments, a second end of the reduction arm is secured to the reduction pawl and constrained within a vertical slot of the main body.

In certain illustrative embodiments, the drive handle actuates one end of the reduction arm in a circular path around a central pivot point.

In certain illustrative embodiments, the main body is adapted to receive a portion of the rod therein.

In certain illustrative embodiments, the reduction pawl provides a reduction force by pulling the ratchet collet into the main body.

In certain illustrative embodiments, actuation of the drive handle provides a firm connection to a spinal screw by closing a proximal end of the ratchet collet over one or more mating features in the head of the spinal screw.

In certain illustrative embodiments, actuation of the drive handle will provide about 6 mm of reduction.

In certain illustrative embodiments, the retention pawl retains the current position of the ratchet collet preventing the loss of reduction.

In certain illustrative embodiments, the when the drive handle is in the fully open position, the reduction pawl rests against the drive release, releasing a tooth engagement from the ratchet collet.

In certain illustrative embodiments, the instrument is suitable to engage and disengage a spinal screw.

In certain illustrative embodiments, the ratchet collet can be adjusted for use with a variety of spinal screw and rod systems including multiple rod diameters and materials.

In certain illustrative embodiments, the retention pawl assembly includes a locking mechanism to remain in a reduced position.

In certain illustrative embodiments, the reduction pawl is spring biased.

In certain illustrative embodiments, the retention pawl is spring biased.

In certain illustrative embodiments, the ratchet collet includes a pair of arms, optionally flexible, extending proximally from said distal end thereof.

In certain illustrative embodiments, the ratchet collet includes one or more prongs at the distal end of each of said arms, each of said prongs defining a channel for receiving the rod therein.

In certain illustrative embodiments, the ratchet collet includes a pair of elongated slots extending between said arms opening at said distal end.

In another embodiment, the invention encompasses a surgical instrument for reducing a rod toward a bone fastener comprising:
  a main body, a drive handle, a reduction arm, a reduction pawl, a retention pawl, a main release, a drive release and ratchet collet,
  wherein the main body comprises a palm handle, a mechanism housing and a collet compressor,
  wherein the drive handle is secured to the main body, directly opposing the main body palm handle, forming an actuating grip assembly,
  wherein the drive handle is secured to a first end of the reduction arm, offset from the central pivot point,
  wherein a second end of the reduction arm is secured to the reduction pawl and constrained within a vertical slot of the main body.

In certain illustrative embodiments, the instrument includes an actuating assembly located within the main body. In certain illustrative embodiments, the actuating assembly includes a reduction arm, a reduction pawl, a retention pawl, and a drive release.

In certain illustrative embodiments, the drive handle actuates one end of the reduction arm in a circular path around the central pivot point.

In certain illustrative embodiments, the main body is adapted to receive a portion of the rod therein.

In certain illustrative embodiments, the reduction pawl provides a reduction force by pulling the ratchet collect into the main body.

In certain illustrative embodiments, actuation of the drive handle provides a firm connection to a spinal screw by closing the proximal end of the ratchet collet over mating features in the head of the spinal screw.

In certain illustrative embodiments, actuation of the drive handle will provide approximately 6 mm of reduction.

In certain illustrative embodiments, the retention pawl retains the current position of the ratchet collet preventing the loss of reduction.

In certain illustrative embodiments, when the drive handle in the fully open position, the reduction pawl rests against the drive release, releasing a tooth engagement from the ratchet collet.

In certain illustrative embodiments, the instrument is suitable to engage and disengage the spinal screw.

In certain illustrative embodiments, the ratchet collet can also be adjusted for use with a variety of spinal screw and rod systems including multiple rod diameters and materials.

In certain illustrative embodiments, the retention pawl assembly includes a locking mechanism to remain in a reduced position.

In certain illustrative embodiments, the retention pawl is spring biased.

In certain illustrative embodiments, the ratchet collet includes a pair of arms, optionally flexible, extending proximally from a distal end thereof.

In certain illustrative embodiments, the ratchet collet includes a prong at the distal end of each of said arms, each of said prongs defining a channel for receiving the rod therein.

In certain illustrative embodiments, the ratchet collet includes a pair of elongated slots extending between said arms opening at said distal end.

In another embodiment, the invention also encompasses a surgical instrument for reducing a rod toward a bone fastener, comprising:
  a main body; a drive handle; a reduction arm; a reduction pawl; a retention pawl; a main release; a drive release; and ratchet collet,
  wherein the main body comprises a palm handle, a mechanism housing and a collet compressor,
  wherein the drive handle is secured to the main body, directly opposing the main body palm handle, forming an actuating grip assembly,
  wherein the drive handle is secured to a first end of the reduction arm, offset from the central pivot point,
  wherein a second end of the reduction arm is secured to the reduction pawl and constrained within a vertical slot of the main body.
  wherein the drive handle actuates one end of the reduction arm in a circular path around the central pivot point.
  wherein said main body is adapted to receive a portion of the rod therein.
  wherein the reduction pawl provides a reduction force by pulling the ratchet collect into the main body.

In another embodiment, the invention also encompasses a method of positioning a rod implant in a patient, comprising: fixing a fastener to a patient; placing a rod implant adjacent said fastener; providing an instrument as described herein; inserting said instrument through an access to said fastener and said implant; engaging a distal portion of the instrument to said fastener; and moving a ratchet collet of said instrument distally so that said ratchet collet contacts said implant and moves said implant toward said fastener.

With reference to FIG. 1, in certain embodiments, the instrument 100 includes a main body 110, which serves a variety of roles in this instrument including a palm handle 115, mechanism housing 113 and collet compressor. The main body 110 extends along a longitudinal axis. The instrument further includes a drive handle 120, which is situated substantially parallel to the main body. In certain embodiments, the drive handle 120 is pinned to the main body 110, directly opposing the main body palm handle 115, forming an actuating grip assembly configured to be received in the hand of the surgeon. Each handle portion 115 or 120 may be integrally formed with the associated shaft or otherwise coupled thereto through any suitable means. The instrument further includes an actuating assembly portion 113 within a central region of the main body, for selectively engaging and inserting a spinal rod into a rod-receiving portion of a selected polyaxial screw or other suitable implant when a user actuates the instrument.

Figure 2:
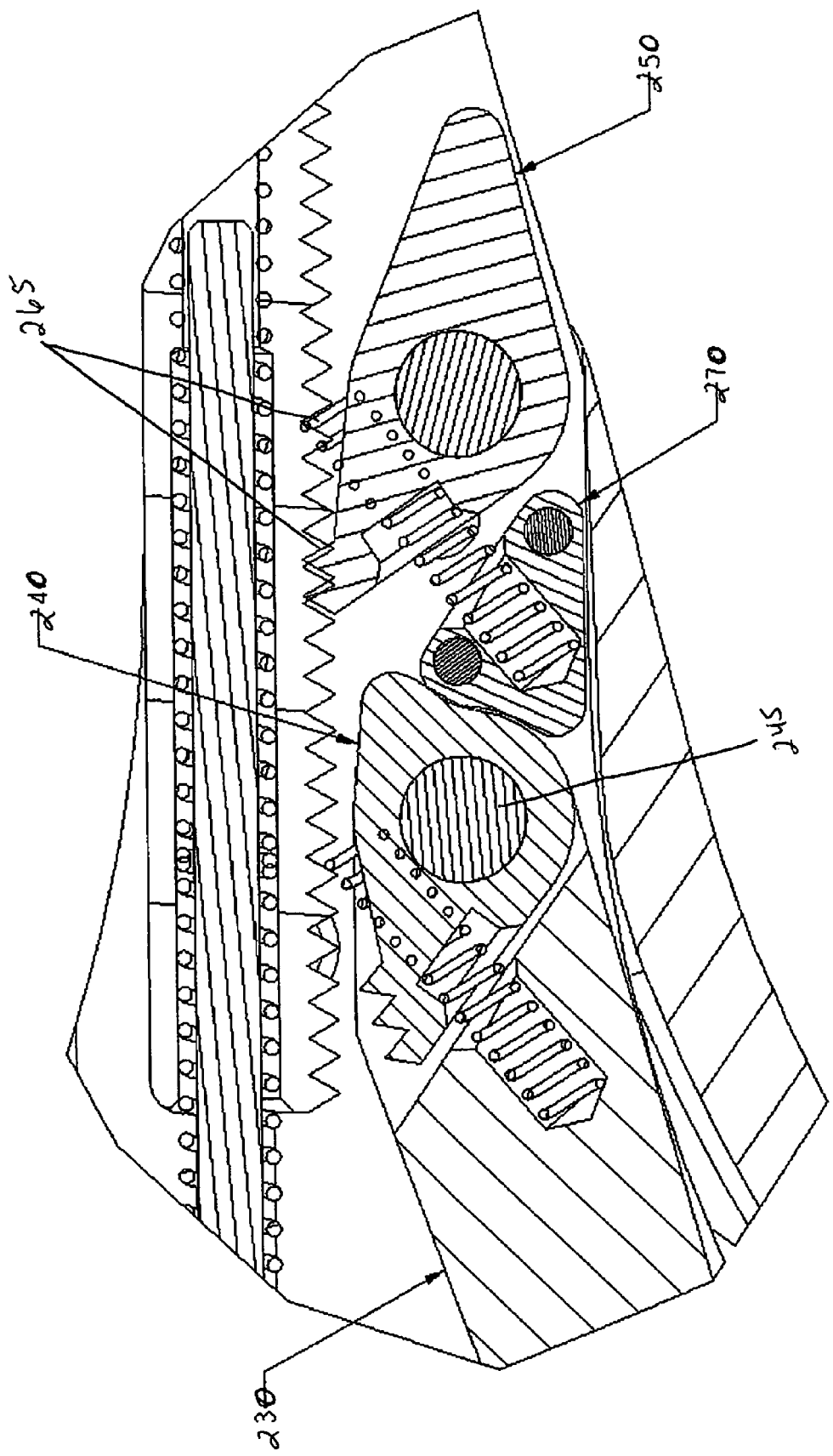
FIG. 2 illustrates an enlarged view of the actuating assembly including the reduction and retention pawl mechanism.
Figure 3:
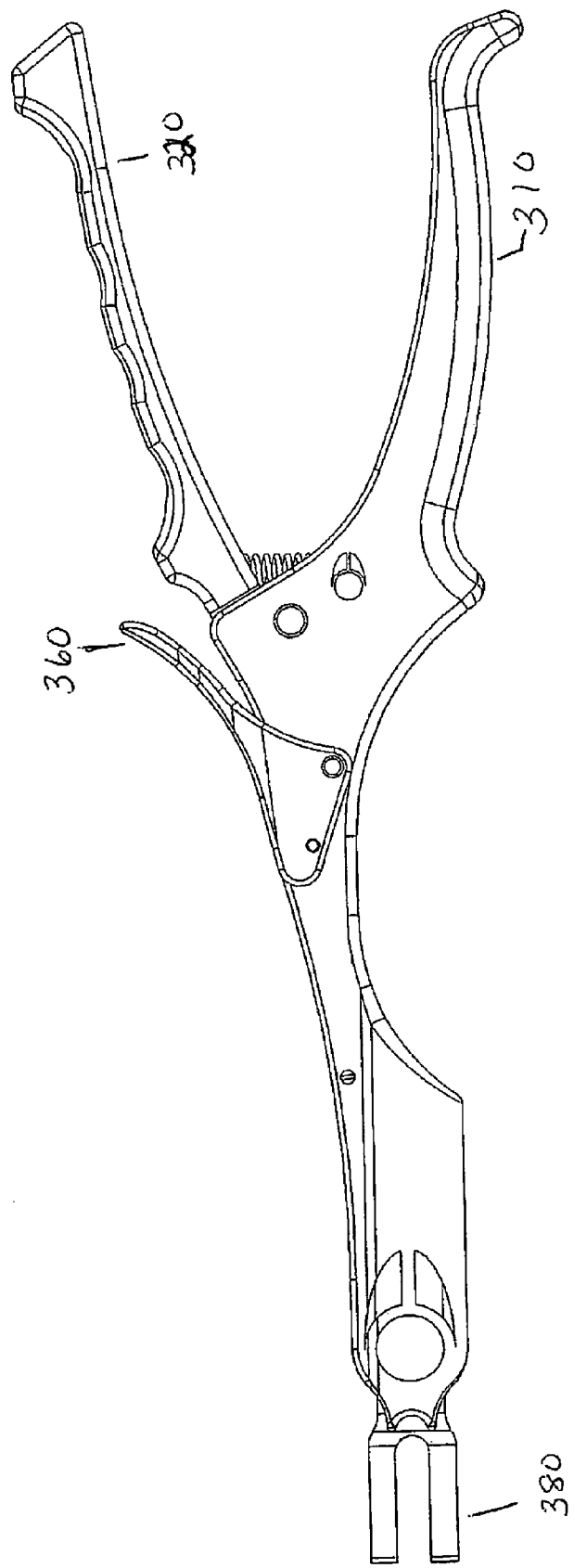
FIG. 3 illustrates a side perspective view of a rod reduction instrument in accordance with one illustrative embodiment of the invention.

With Reference to FIGS. 1 and 2, in certain embodiments, the drive handle 120 is secured 190 (e.g., pinned) to a first end of the reduction arm 230, offset from the central pivot point. In certain embodiments, a second end of the reduction arm is pinned to a reduction pawl 240 and constrained within a vertical slot of the main body 110. In certain embodiments, actuating the drive handle 120 pulls one end of the reduction arm 230 in a circular path around the central pivot point. The instrument includes a spring extending between reduction arm 230 and reduction pawl 240 to provide a biasing force, for example, a biasing force in the open or closed direction. In certain embodiments, the vertical component of that motion is transferred directly to the reduction pawl 240, which is constrained to a vertical path within the main body. In certain embodiments, the vertical motion of the reduction pawl 240 provides a reduction force by pulling the ratchet collect 180 into the main body. In certain embodiments, the initial actuation of the drive handle 120 provides a firm connection to the spinal screw by closing the proximal end of the ratchet collet 180 over mating features in the head of the spinal screw. In certain embodiments, each pull of the drive handle 120 will provide about 6 mm of reduction. In alternate embodiments, more or less reduction distance may be provided. In one non-limiting example, in certain embodiments full actuation may be 6 mm whereas partial actuation may be less. In certain embodiments, after each pull of the drive handle, the retention pawl 250 will retain the current position of the ratchet collet 180, preventing the loss of reduction.

According to an illustrative embodiment, the actuating assembly is illustrated in FIG. 2. The actuating assembly is actuated by moving the drive handle 120 relative to the main body palm handle 115. In an illustrative embodiment, the drive handle 120 relative to the main body palm handle 115 move relative to each other by moving the drive handle 120 relative to the main body palm handle 115, for example, by squeezing to bring the handles 115, 120 toward each other. One skilled in the art will recognize that any suitable actuation means may be used. For example, in one non-limiting alternate embodiment, a cylindrical ratcheting or pawl and or drive mechanism may be used.

The instrument may have any suitable size and shape and may be formed on any suitable surgical material, such as titanium, stainless steel and other surgical materials known in the art. The instrument preferably has a sufficient length so as to enable the distal end to be placed adjacent to a surgical site, while proximal end remains outside the patient's body and accessible by the surgeon.

In certain embodiments, when the drive handle 120 is in the fully open position, the reduction pawl rests against the drive release 270, releasing the tooth engagement 265 from the ratchet collet 180. This allows the instrument to be released with the pull of the main release 160, which actuates the retention pawl 250, releasing the tooth engagement 265 from the ratchet collet 180. The design of the ratchet collet 180 and reduction pawl 240 allow for the instrument to easily engage and disengage the spinal screw, while quickly reducing the time needed for full reduction. If a minimal amount of reduction is required, a simple push of the main body can remove unnecessary travel in the reduction mechanism. In certain embodiments, the ratchet collet 180 can also be adjusted to be used with a variety of spinal screw and rod systems including multiple rod diameters and materials. To facilitate disengagement of ratchet collet, a main release lever 160 is provided. When retention pawl 250 in the closed position, main release can be pushed, thereby raising drive release 270 and lifting retention pawl 250 to return to the open position.

This instrument provides a quick and ergonomic solution to surgical reduction needs. In certain embodiments, silicon grips are included in the ergonomically cut drive handle to increase surgeon comfort during use. The instrument allows for large amounts of reduction without excessive applied force. In certain embodiments, the instrument gearing can be adjusted to increase or decrease mechanical advantage.

The invention encompasses instruments offered in a variety of orientations depending on surgeon needs including overhead (in-line) and pistol-grip (90 degree offset), including any degree offset between.

Referring to FIGS. 1-7, there is shown an illustrative embodiment of a rod reducer instrument according to the invention. In normal use in the patient's body the rod reducer instrument is oriented so that its actuator assembly is located proximally, and accessible by the surgeon, and the opposite end of instrument is oriented distally away from the surgeon and towards the operative site. The operative site is, for example, a vertebral body of the spinal column in which a fastener is engaged. In order to facilitate the surgeon's positioning of a rod in a fastener, the rod reducer instrument 100 is engageable to a fastener and positionable against the rod and thereafter operable to move the rod in closer proximity to the fastener such that the rod can be secured to the fastener. The fastener can be a multi-axial or uni-axial screw, a hook, or other bone or tissue engaging device. The rod can be any elongated implant element of any size or shape so long as it can be secured to fastener.

Figure 4:
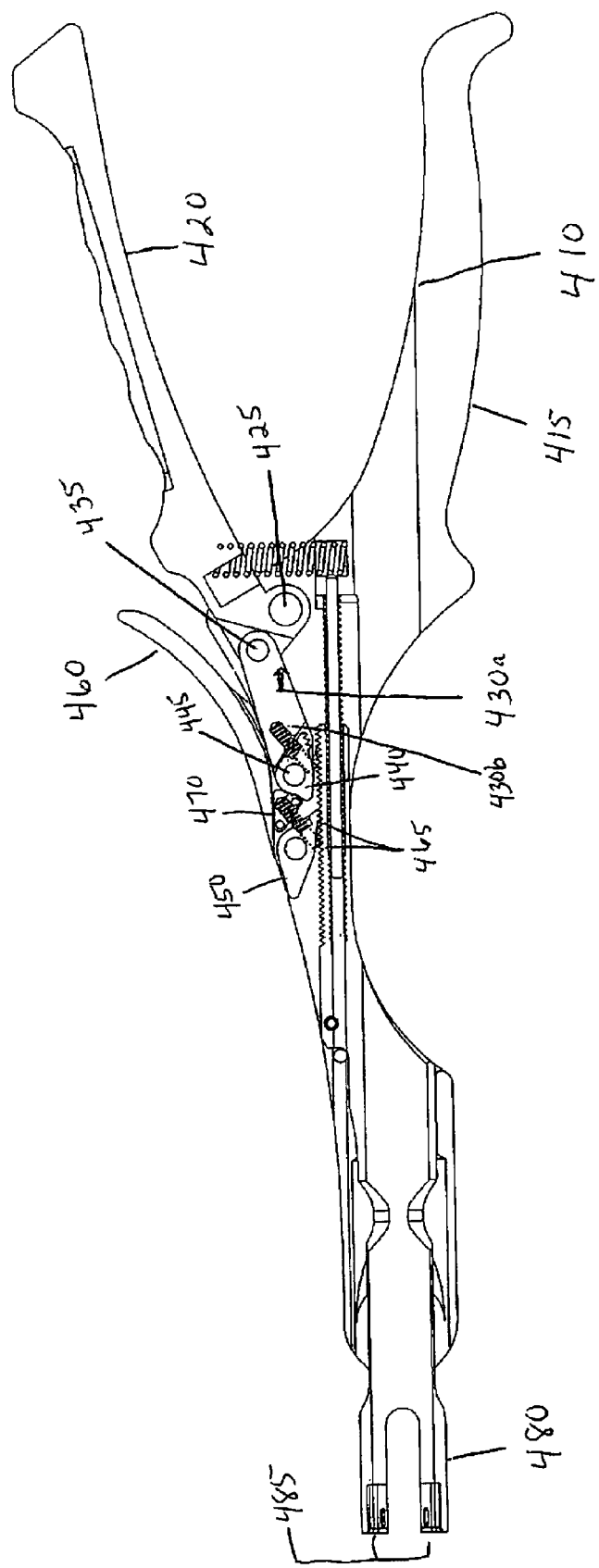
FIG. 4 illustrates a cross-sectional view of a rod reduction instrument including a view of a reduction and retention pawl mechanism in accordance with one illustrative embodiment of the invention.
Figure 5:
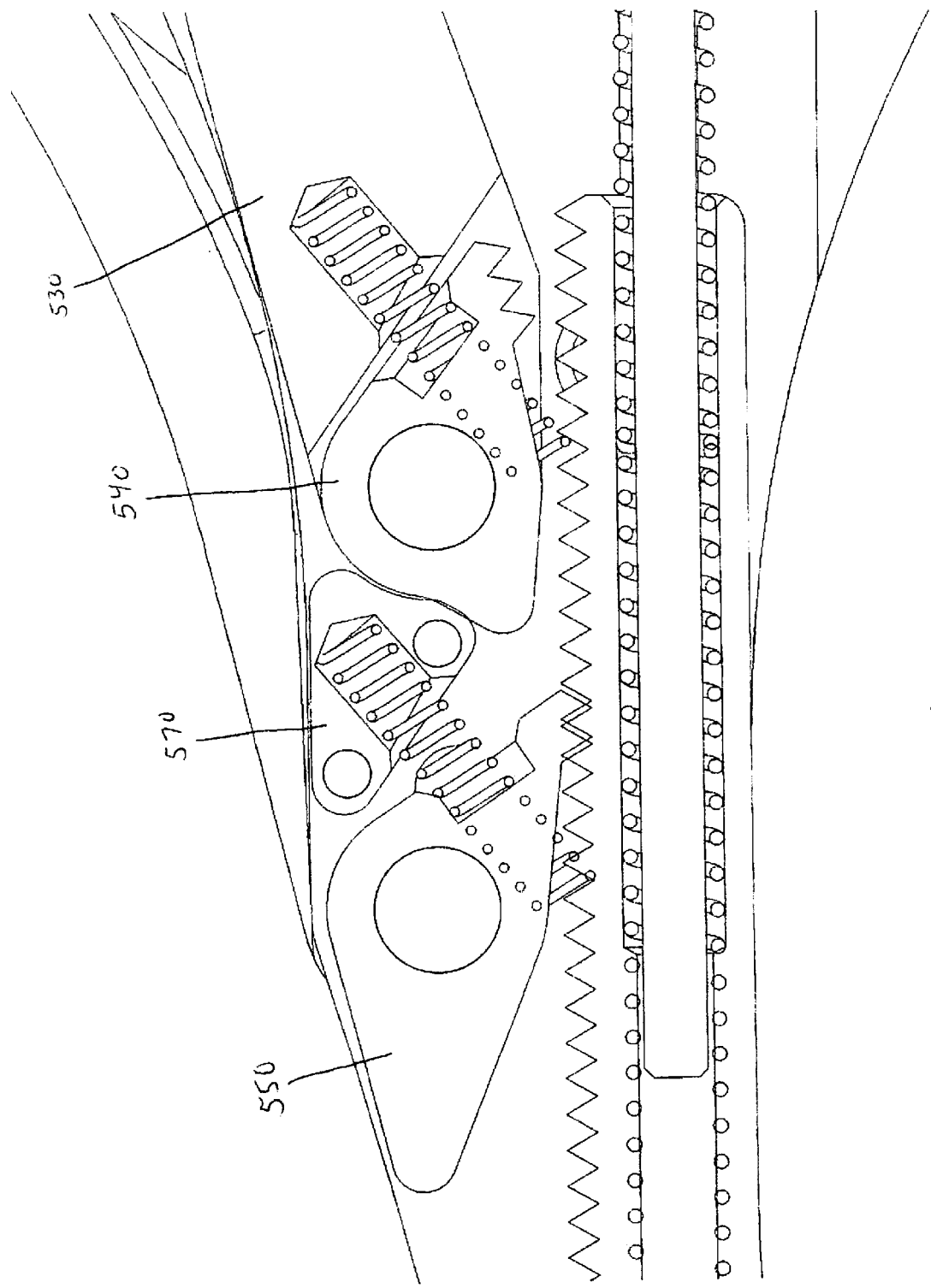
FIG. 5 illustrates an enlarged view of the actuating assembly including the reduction and retention pawl mechanism.

With reference to FIGS. 2 and 5, the actuating assembly can further include a drive release mechanism 270 and 570 respectively, for forcing the engagement mechanism to release the implant, for example, by pressing the main release, when necessary, for example, after insertion of a rod. The actuating assembly portion of the instrument is not limited to the embodiments described relative to FIGS. 1-7. One of ordinary skill in the art will recognize that the actuating assembly may have any size, shape and configuration suitable for engaging and inserting a spinal rod into a rod-receiving portion of an implant. The instrument may further include a biasing element, such as a spring, disposed between relatively movable elements to bias the instrument to a default position, as illustrated for example, in FIGS. 2 and 5. The biasing element may be located between the handle members. For example, FIG. 4 shows a spring between the handles 415, 420 for biasing the handles 415, 420 in a selected position relative to each other. In addition, the actuating assembly in FIG. 4 can include a biasing spring between the reduction arm 430 and reduction pawl 445 and/or the drive release 470 and the retention pawl 450.

With reference to FIG. 4, in certain embodiments, the main body 410 includes a palm handle 415, mechanism housing (i.e., also referred herein as actuating assembly) and collet compressor. In certain embodiments, the drive handle 420 is pinned 425 to the main body 410, directly opposing the main body palm handle 415, forming an actuating grip assembly. In certain embodiments, the drive handle 420 is secured 435 to a first end of the reduction arm 430*a*, offset from the central pivot point. In certain embodiments, a second end of the reduction arm 430*b* is secured 445 to a reduction pawl 440 and constrained within a vertical slot of the main body 410. In certain embodiments, actuating the drive handle 420 pulls one end of the reduction arm 430*a/b* in a circular path around the central pivot point. In certain embodiments, the vertical component of that motion is transferred directly to the reduction pawl 440, which is constrained to a vertical path within the main body. In certain embodiments, the vertical motion of the reduction pawl 440 provides a reduction force by pulling the ratchet collect 480 into the main body. In certain embodiments, the initial actuation of the drive handle 420 provides a firm connection to the spinal screw by closing the proximal end of the ratchet collet 480 over mating features in the head of the spinal screw. The ratchet collet 480 optionally has mating features 485 that correspond to a spinal screw or rod. In certain embodiments, each pull of the drive handle 420 will provide about 6 mm or reduction. In certain embodiments, the instrument gearing can be adjusted to increase or decrease mechanical advantage. In certain embodiments, after each pull of the drive handle 420, the retention pawl 450 will retain the current position of the ratchet collet 480, preventing the loss of reduction.

With Reference to FIG. 5, in certain embodiments, the drive handle (not illustrated in FIG. 5) is pinned to a first end of the reduction arm 530, offset from the central pivot point. In certain embodiments, a second end of the reduction arm is pinned to a reduction pawl 540. In certain embodiments, actuating the drive handle pulls one end of the reduction arm 530 in a circular path around the central pivot point. In certain embodiments, the vertical component of that motion is transferred directly to the reduction pawl 540, which is constrained to a vertical path within the main body. In certain embodiments, the vertical motion of the reduction pawl 540 provides a reduction force by pulling the ratchet collect into the main body.

Figure 6:
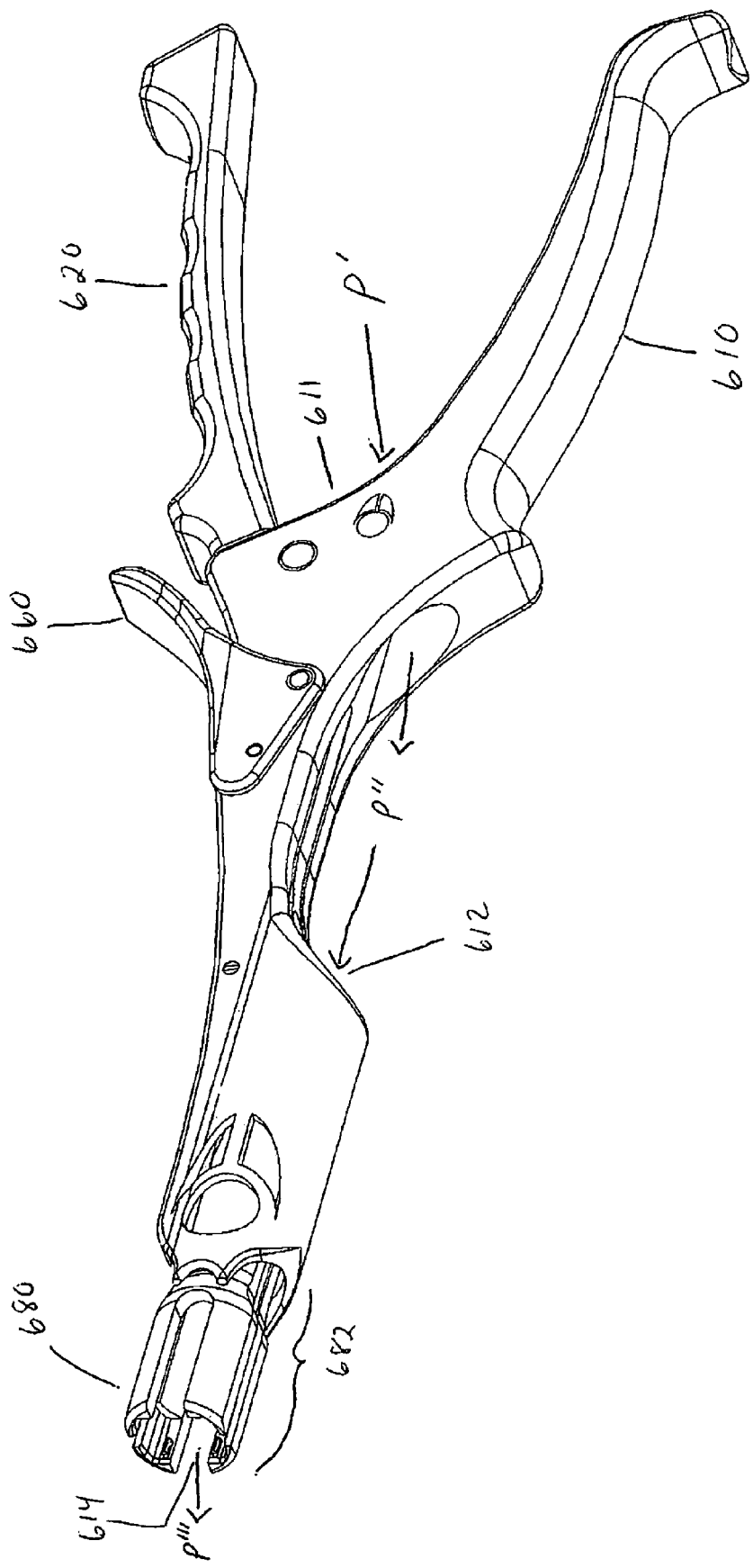
FIG. 6 illustrates a side perspective view of a rod reducer instrument in accordance with one illustrative embodiment of the invention.

With reference to FIG. 6, ratchet collet 680 includes a body 682 having a longitudinal axis and an enlarged distal portion. Although body 682 is shown as having a generally cylindrical cross-section perpendicular to axis, it is understood that body 682 can have a cross-section of any appropriate shape, such as oval, square, or regularly or irregularly polygonal. Body 682 is hollow in certain embodiments, having passage extending between and opening at a proximal end and a distal end of body 682. Body 682 also includes prongs at a distal end. Each prong includes a rod channel configured to receive a rod therein. Prongs can be squeezed together by reducing member contacting the enlarged distal portion to hold a fastener therein, and released to move apart from each other and release fastener. Alternatively, prongs can be forced apart by insertion of a fixation element or other application of force, and will naturally clamp on or around a fastener. It will be understood that ratchet collet 680 need not include prongs but rather can be a formed from a substantially solid body having an appropriately-shaped socket distal end for engaging a fastener and including a rod channel, which receives a rod.

Referring to FIG. 6, in certain embodiments, ratchet collet 680 includes a substantially cylindrical body extending between a proximal end and a distal end. Ratchet collet member 680 also includes internal channels P' and P'" extending along longitudinal axis of the main body between and opening at proximal end of the main body 612 and distal end 614. In certain embodiments, channel P can include distal portion P''''. In certain embodiments, channel P also includes a proximal portion P' in communication with distal portion and opening at proximal end. In certain embodiments, distal portion 614 is larger in diameter than proximal portion 611 and is sized to receive enlarged distal portion. The length passage can vary from 10 millimeters up to 20 centimeters or more, thus allowing the surgeon to select a rod reducer instrument having an extension and passage of appropriate length for the distance of rod reduction beyond distal end that is desired.

Figure 7:
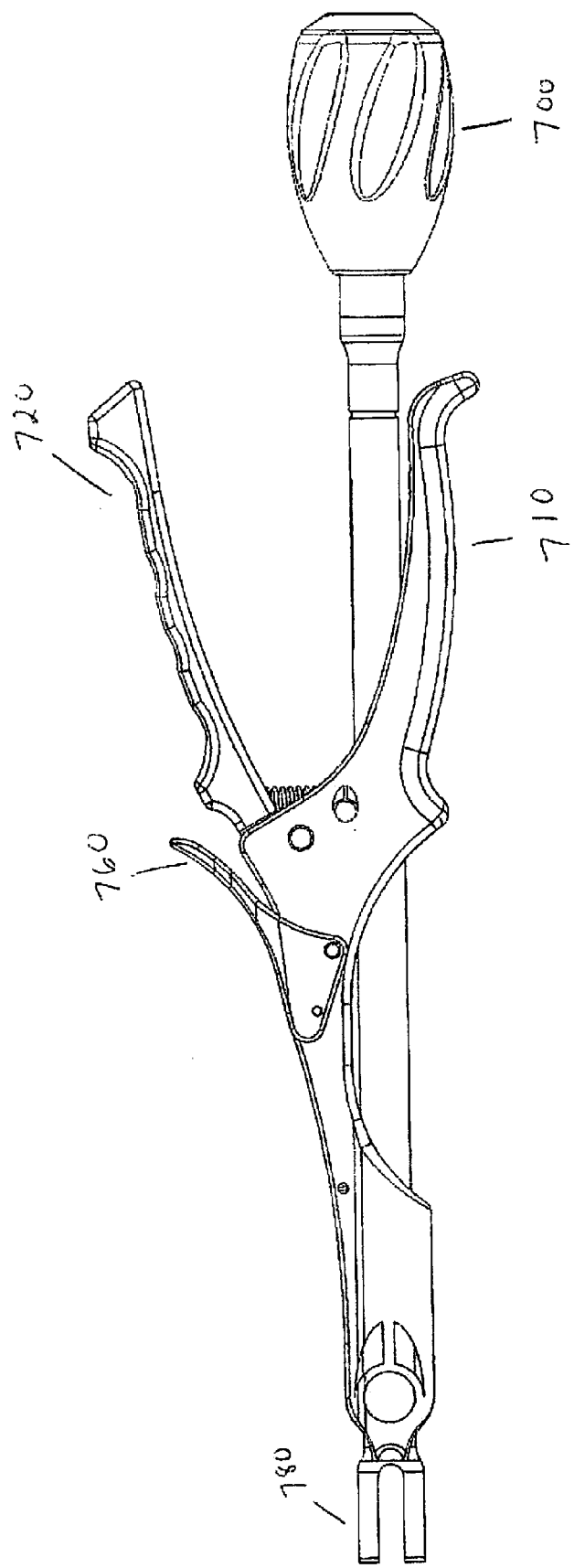
FIG. 7 illustrates a side perspective view of a rod reducer instrument in accordance with one illustrative embodiment of the invention.

FIG. 7 illustrates a rod reducing instrument of the invention including a driver is inserted through the rod reducer internal passage to insert a locking cap into the head of the pedicle screw. In certain embodiments, a driver may be used to temporarily lock and secure a rod and implant construct. In certain embodiments, temporary fixation of the implant may be performed numerous times without damage to either the plug or the implant threads. The instrument also includes a ratchet collet, for selectively locking the instrument in the closed position so that the rod reducer will continue to apply a force to the rod without requiring the user to hold the instrument in the closed position. One skilled in the art will recognize that any suitable means for selectively locking the instrument in a selected position may be used.

The instruments of the present invention are preferably made of a sturdy biocompatible material such as titanium or stainless steel using standard fabrication techniques for medical grade instruments. However, other biocompatible materials are also contemplated.

In the specification, there have been disclosed typical illustrative embodiments of the invention and, although specific terms are employed, they are used in a generic and descriptive sense only and not for purposes of limitation. Obviously many modifications and variations of the invention are possible in light of the above teachings. It is therefore to be understood that the invention may be practiced otherwise than as specifically described.

Unless defined otherwise, all technical and scientific terms and any acronyms used herein have the same meanings as commonly understood by one of ordinary skill in the art in the field of this invention. Although any compositions, methods, kits, and means for communicating information similar or equivalent to those described herein can be used to practice this invention, the preferred compositions, methods, kits, and means for communicating information are described herein.

What is claimed is:

1. An orthopedic instrument for reducing a rod comprising:
a main body;
a drive handle connected to the main body, wherein the main body houses:
a reduction arm having a first end and a second end, the first end connected to the drive handle and a second end connected to a reduction pawl, wherein the reduction pawl is configured to pull a ratchet collet into the main body by pulling the drive handle thereby resulting in a reduction of an implant;
a retention pawl for maintaining the position of the ratchet collet following reduction; and
a drive release,
wherein when the drive handle is in a first position, the reduction pawl rests against the drive release and the retention pawl is capable of actuation.

2. The instrument of claim 1, wherein the main body comprises a palm handle, an actuating assembly, and a collet compressor.

3. The instrument of claim 1, wherein the drive handle is secured to the main body, directly opposing the main body palm handle, forming an actuating grip assembly.

4. The instrument of claim 1, wherein the drive handle is secured to a first end of the reduction arm, offset from a central pivot point.

5. The instrument of claim 1, wherein a second end of the reduction arm is secured to the reduction pawl and constrained within a vertical slot of the main body.

6. The instrument of claim 1, wherein the drive handle actuates one end of the reduction arm in a circular path around a central pivot point.

7. The instrument of claim 1, wherein said main body is adapted to receive a portion of the rod therein.

8. The instrument of claim 1, wherein the reduction pawl provides a reduction force by pulling the ratchet collect into the main body.

9. The instrument of claim 1, wherein actuation of the drive handle provides a firm connection to a spinal screw by closing a proximal end of the ratchet collet over one or more mating features in the head of the spinal screw.

10. The instrument of claim 1, wherein actuation of the drive handle will provide about 6 mm of reduction.

11. The instrument of claim 1, wherein the retention pawl retains the current position of the ratchet collet preventing the loss of reduction.

12. The instrument of claim 1, wherein when the drive handle is in the fully open position, the reduction pawl rests against the drive release, releasing a tooth engagement from the ratchet collet.

13. The instrument of claim 1, wherein the instrument is suitable to engage and disengage a spinal screw.

14. The instrument of claim 1, wherein the ratchet collet can be adjusted for use with a variety of spinal screw and rod systems including multiple rod diameters and materials.

15. The instrument of claim 1, wherein said retention pawl assembly includes a locking mechanism to remain in a reduced position.

16. The instrument of claim 1, wherein said retention pawl is spring biased.

17. The instrument of claim 1, wherein said ratchet collet includes a pair of arms extending proximally from said distal end thereof.

18. The instrument of claim 17, wherein said ratchet collet includes one or more prongs at the distal end of each of said arms, each of said prongs defining a channel for receiving the rod therein.

19. The instrument of claim 17, wherein said ratchet collet includes a pair of elongated slots extending between said arms opening at said distal end.

20. A surgical instrument for reducing a rod toward a bone fastener comprising:
a main body,
a drive handle connected to the main body, wherein the main body houses:
a reduction arm having a first end and a second end, the first end connected to the drive handle and a second end connected to a reduction pawl, wherein the reduction pawl is configured to pull a ratchet collet into the main body by pulling the drive handle thereby resulting in a reduction of an implant;
a retention pawl for maintaining the position of the ratchet collet following reduction,
a main release configured to actuate the retention pawl, and
a drive release,
wherein when the drive handle is in a first position, the reduction pawl rests against the drive release and the retention pawl is capable of actuation.

21. The instrument of claim 20, wherein the drive handle actuates one end of the reduction arm in a circular path around the central pivot point.

22. The instrument of claim 20, wherein said main body is adapted to receive a portion of the rod therein.

23. The instrument of claim 20, wherein the reduction pawl provides a reduction force by pulling the ratchet collect into the main body.

24. The instrument of claim 20, wherein actuation of the drive handle provides a firm connection to a spinal screw by closing the proximal end of the ratchet collet over mating features in the head of the spinal screw.

25. The instrument of claim 20, wherein actuation of the drive handle will provide approximately 6 mm or reduction.

26. The instrument of claim 20, wherein the retention pawl retains the current position of the ratchet collet preventing the loss of reduction.

27. The instrument of claim 20, wherein when the drive handle in the fully open position, the reduction pawl rests against the drive release, releasing a tooth engagement from the ratchet collet.

28. The instrument of claim 20, wherein the instrument is suitable to engage and disengage the spinal screw.

29. The instrument of claim 20, wherein the ratchet collet can also be adjusted for use with a variety of spinal screw and rod systems including multiple rod diameters and materials.

30. The instrument of claim 20, wherein said retention pawl assembly includes a locking mechanism to remain in a reduced position.

31. The instrument of claim 20, wherein said retention pawl is spring biased.

32. The instrument of claim 20, wherein said ratchet collet includes a pair of arms extending proximally from a distal end thereof.

33. The instrument of claim 32, wherein said ratchet collet includes a prong at the distal end of each of said arms, each of said prongs defining a channel for receiving the rod therein.

34. The instrument of claim 32, wherein said ratchet collet includes a pair of elongated slots extending between said arms opening at said distal end.

35. A surgical instrument for reducing a rod toward a bone fastener, comprising:
a main body;
a drive handle connected to the main body, wherein the main body houses:
a reduction arm having a first end and a second end, the first end connected to the drive handle and a second end connected to a reduction pawl, wherein the reduction pawl is configured to pull a ratchet collet into the main body by pulling the drive handle thereby resulting in a reduction of an implant;
a retention pawl for maintaining the position of the ratchet collet following reduction; and
a drive release;
wherein when the drive handle is in a first position, the reduction pawl rests against the drive release and the retention pawl is capable of actuation,
wherein the main body comprises a palm handle, a mechanism housing and a collet compressor, wherein the drive handle is secured to the main body, directly opposing the main body palm handle, forming an actuating grip assembly, wherein the drive handle is secured to a first end of the reduction arm, offset from the central pivot point, wherein a second end of the reduction arm is secured to the reduction pawl and constrained within a vertical slot of the main body, wherein the drive handle actuates one end of the reduction arm in a circular path around the central pivot point, wherein said main body is adapted to receive a portion of the rod therein.

* * * * *